United States Patent
Mohan et al.

(10) Patent No.: US 10,690,683 B2
(45) Date of Patent: Jun. 23, 2020

(54) METHODS OF USE FOR INTERMEDIATE FILAMENT PROTEIN PROBES

(71) Applicant: University of Connecticut, Farmington, CT (US)

(72) Inventors: Royce Mohan, Farmington, CT (US); Paola Bargagna-Mohan, Farmington, CT (US); Dennis L. Wright, Farmington, CT (US); Santosh Keshipeddy, Farmington, CT (US)

(73) Assignee: University of Conneticut, Farmington, CT (US)

( * ) Notice: Subject to any disclaimer, the term of this patent is extended or adjusted under 35 U.S.C. 154(b) by 0 days.

(21) Appl. No.: 15/675,353

(22) Filed: Aug. 11, 2017

(65) Prior Publication Data
US 2018/0045738 A1    Feb. 15, 2018

Related U.S. Application Data

(60) Provisional application No. 62/374,376, filed on Aug. 12, 2016.

(51) Int. Cl.
| | | |
|---|---|---|
| G01N 33/68 | (2006.01) | |
| G01N 33/50 | (2006.01) | |
| G01N 33/58 | (2006.01) | |

(52) U.S. Cl.
CPC ..... *G01N 33/6893* (2013.01); *G01N 33/5005* (2013.01); *G01N 33/582* (2013.01); *G01N 2333/47* (2013.01); *G01N 2800/16* (2013.01); *G01N 2800/164* (2013.01); *G01N 2800/168* (2013.01)

(58) Field of Classification Search
None
See application file for complete search history.

(56) References Cited

U.S. PATENT DOCUMENTS

| | | |
|---|---|---|
| 8,283,323 B2 | 10/2012 | Mohan et al. |
| 8,481,752 B2 | 7/2013 | Xu et al. |
| 8,598,339 B2 | 12/2013 | Timmermann et al. |
| 8,685,372 B2 | 4/2014 | Tsien et al. |
| 8,735,178 B2 * | 5/2014 | Mohan ............ B09C 1/08 436/544 |
| 8,802,235 B2 | 8/2014 | Forrest et al. |
| 8,927,719 B2 | 1/2015 | Xu et al. |
| 9,072,773 B2 | 7/2015 | Gonzalez et al. |
| 2015/0050212 A1 * | 2/2015 | Low ............ C07D 405/12 424/1.69 |

OTHER PUBLICATIONS

Ren et al., Early Detection and Treatment of Wear Particle-Induced Inflammation and Bone Loss in a Mouse Calvarial Osteolysis Model Using HPMA Copolymer Conjugates, 2011, Molecular Pharmaceutics, vol. 8, pp. 1043-1051. (Year: 2011).*

Korb et al., Use of monoclonal antibody-IRDye800CW bioconjugates in the resection of breast cancer, 2014, Journal of Surgical Research, vol. 188, pp. 119-128. (Year: 2013).*

Bargagna-Mohan et al., "Corneal antifibrotic switch identified in genetic and pharmacological deficiency of vimentin," J Biol Chem., 2012; 287: 989-1006.

Bargagna-Mohan et al., "Vimentin phosphorylation underlies myofibroblast sensitivity to Withaferin A in vitro and during corneal fibrosis," PLoS One, 2015; 10:e0133399, 26 pages.

Bargagna-Mohan et al., "Withaterin A—Effectively targets soluble vimentin in the glaucoma filtration surgical mode of fibrosis," PLoS One, 2013; 8:e63881, 14 pages.

Bargagna-Mohan et al., "Withaterin A—Targets intermediate filaments glial fibrillary acidic protein and vimentin in a model of retinal gliosis," J Biol Chem., 2010; 285:7657-7669.

Chang et al., "The dynamic properties of intermediate filaments during organelle transport," J Cell Sci., 2009; 122: 2914-2923.

Eriksson et al., "Specific in vivo phosphorylation sites determine the assembly dynamics of vimentin intermediate filaments," J Cell Sci., 2004; 117: 919-932.

Giani et al., "In vivo evaluation of laser-induced choroidal neovascularization using spectral-domain optical coherence tomography," Invest Ophthalmol Vis Sci., 2011; 52: 3880-3887.

Helfand et al., "Intermediate filaments are dynamic and motile elements of cellular architecture," J Cell Sci., 2004; 117: 133-141.

Helfand et al., "Vimentin organization modulates the formation of lamellipodia," Mol Biol Cell., 2011; 22: 1274-1289.

Hermann et al., "Structure, assembly, and dynamics of intermediate filaments," Subcell Biochem., 1998; 31: 319-362.

Hookway et al., "Microtubule-dependent transport and dynamics of vimentin intermediate filaments," Mol Biol Cell., 2015; 26: 1675-1686.

Lukinavičius et al., "Fluorogenic probes for live-cell imaging of the cytoskeleton," Nat Methods, 2014; 11(7):731-3.

Luo et al., "A review of NIR dyes in cancer targeting and imaging," Biomaterials, 2011; 32: 7127-7138.

Mendez et al., "Vimentin induces changes in cell shape, motility, and adhesion during the epithelial to mesenchymal transition" Faseb J., 2010; 24: 1838-1851.

Mohan et al., "A Novel Vimentin-Targeting Probe for Imaging Ocular Fibrosis," power point presentation with abstract (2016) 3 pages, University of Connecticut.

Mohan et al., "An Intermediate Filament Probe to Illuminate Preclinical Retinal Gliosis in AMD," power point presentation with abstract (2016) 4 pages, University of Connecticut.

Mohan et al., "Imaging Withaferin A—Vimentin Interactions in Live Cells and Fibrotic Tissues," power point slide, (2016) 1 page, University of Connecticut.

Mohan et al., "The Use of Withaferin A to Study Intermediate Filaments," Methods Enzymol., 2016; 568: 187-218.

Mohan, "Experimental Biology—Transforming the Future Through Science," abstract (2016) http://submissions.mirasmart.com/EB2016/Proofread.aspx.

Nekrasova et al., "Vimentin intermediate filaments modulate the motility of mitochondria," Mol Bid Cell. 2011; 22(13):2282-9.

(Continued)

*Primary Examiner* — Kevin E Weddington
(74) *Attorney, Agent, or Firm* — Michael Best & Friedrich LLP

(57) ABSTRACT

The present disclosure relates to compounds and methods for labeling and/or detecting proteins in vivo, and methods for probing mitochondrial structure and/or dynamics.

13 Claims, 8 Drawing Sheets

(56) References Cited

OTHER PUBLICATIONS

Prahlad et al., "Rapid movements of vimentin on microtubule tracks: kinesin-dependent assembly of intermediate filament networks," J Cell Biol., 1998; 143: 159-170.
Ridge, et al., "Methods in Enzymology—Chapter Fourteen—Methods for Determining the Cellular Functions of Vimentin Intermediate Filaments," Methods in Enzymology, 2016; 568: 389-426.
Robert et al., "Vimentin filament precursors exchange subunits in an ATP-dependent manner," Proc Natl Acad Sci USA, 2015; 112: E3505-3514.
Sihag et al., "Role of phosphorylation on the structural dynamics and function of types III and IV intermediate filaments," Exp Cell Res., 2007; 313: 2098-2109.
Tackenberg et al., "Muller cell activation, proliferation and migration following laser injury," Mol Vis., 2009; 15: 1886-1896.
Vikstrom et al, "Dynamic aspects of intermediate filament networks in BHK-21 cells" Proc Natl Acad Sci USA, 1989; 86: 549-553.
Vikstrom et al., "Steady state dynamics of intermediate filament networks," J Cell Biol., 1992; 118: 121-129.
Yokota et al., "Development of withaferin A analogs as probes of angiogenesis," Bioorg Med Chem Lett., 2006; 16: 2603-2607.
Zhou et al., "MRI detection of breast cancer micrometastases with a fibronectin-targeting contrast agent," Nat Commun., 2015; 6: 7984.

\* cited by examiner

METHODS OF USE FOR INTERMEDIATE FILAMENT PROTEIN PROBES

CROSS-REFERENCE TO RELATED APPLICATIONS

This application claims priority to U.S. Provisional Application No. 62/374,376, filed Aug. 12, 2016, which is herein incorporated by reference in its entirety.

STATEMENT OF GOVERNMENT INTEREST

This invention was made with government support under grant number R01 EY016782 awarded by the National Institutes of Health. The government has certain rights in the invention.

TECHNICAL FIELD

The present disclosure relates to compounds and methods for labeling and/or detecting proteins in vivo, and methods for probing mitochondrial structure and/or dynamics.

BACKGROUND

There is a continuing need for small molecule probes that selectively target certain forms of complex proteins to study their functions.

SUMMARY

In one aspect, disclosed herein is a method of detecting a type III intermediate filament protein in a subject, the method comprising:

administering to the subject a compound of formula (I)

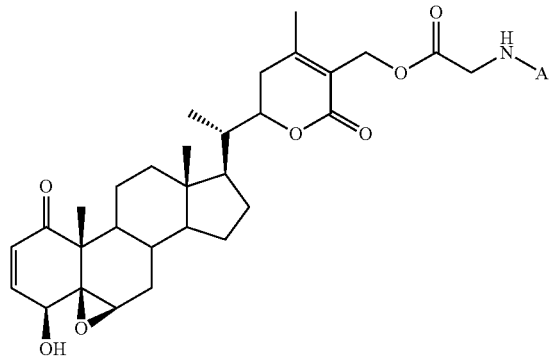

(I)

wherein:
A is a fluorophore;
obtaining a tissue sample from the subject; and
detecting the compound of formula (I) in the tissue sample using fluorescence or near-infrared imaging.

In one aspect, disclosed herein is method of detecting a gliotic condition in a subject, comprising:

administering to the subject a compound of formula (I)

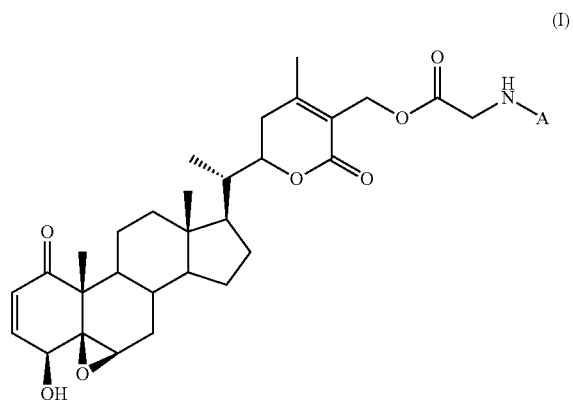

(I)

wherein:
A is a fluorophore;
obtaining a tissue sample from the subject; and
detecting the compound of formula (I) in the tissue sample using fluorescence or near-infrared imaging.

In one aspect, disclosed herein is a method of detecting myofibroblasts in a subject, comprising:

administering to the subject a compound of formula (I)

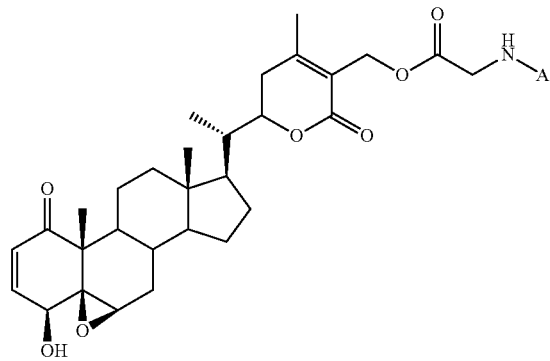

(I)

wherein:
A is a fluorophore;

obtaining a tissue sample from the subject; and detecting the compound of formula (I) in the tissue sample using fluorescence or near-infrared imaging.

In one aspect, disclosed herein is a method of probing mitochondrial structure and dynamics in a cell, the method comprising:

contacting the cell with a compound of formula (I):

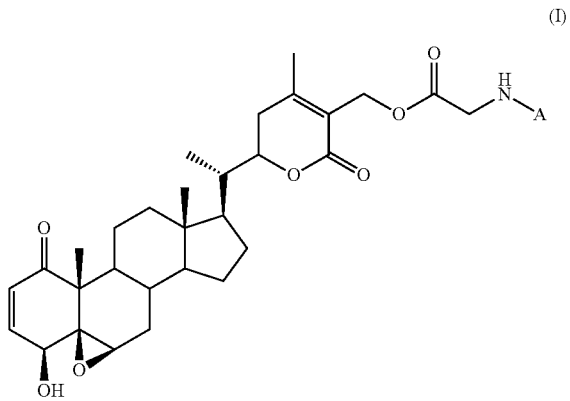

wherein:
A is a fluorophore;
and detecting the compound of formula (I) in the cell using fluorescence or near-infrared imaging.

Other aspects and embodiments of the disclosure will become apparent in light of the following description and drawings.

DETAILED DESCRIPTION

Figure 1:
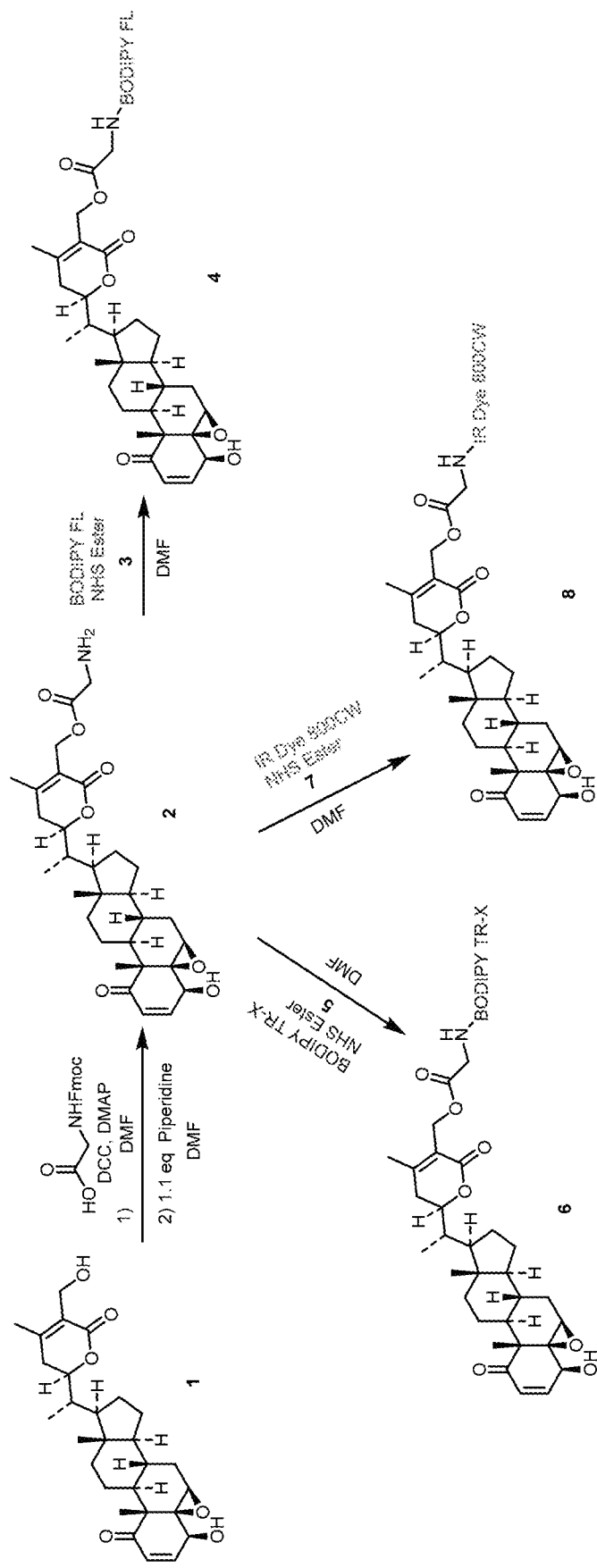
FIG. 1 shows synthetic methods for preparing compounds described herein.

Age-related macular degeneration (AMD) is the leading cause of blindness in developed nations where the late stage, wet form of the disease is managed by anti-angiogenic therapeutics. It is known that if treatment is initiated at the earliest onset of wet-AMD patients face the most favorable outcomes. Currently, there is an urgent unmet medical need for imaging protein biomarkers that can provide information regarding suitable pre-clinical disease states that closely precede the onset of wet-AMD.

The retinal Muller glia are stress responsive cells that become activated and overexpress the glial type III intermediate filaments (IF) around invasive choroidal blood vessels. These proteins are thus potential endogenous reporter systems for wet-AMD. Disclosed herein are methods of using a compound that is a type III IF biomarker probe. Also disclosed herein is a method of detecting reactive Muller glia at a lesion site in a mouse model of wet-AMD, where a laser injury is employed to cause damage to the retina. Delivery of a compound of formula (I) described herein results in labeling of reactive Muller glia at the lesion site. This discovery opens up a new paradigm for biomarker imaging for retinal fibrotic diseases, because such probes can also be efficiently developed for human use.

Additionally, vimentin has numerous cellular functions as this protein class is highly complex in its dynamics and expression. One such function is an association of vimentin with mitochondria, but this fraction of vimentin-associated with mitochondria is only a subset of the bulk of cytoplasmic vimentin. Probe compounds described herein can label vimentin that is associated with mitochondria in a manner that is visually clear and distinct, providing a method to probe mitochondrial dynamics and study the contribution of vimentin sub-species responsible for targeting mitochondria.

1. Definitions

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

As used herein, the term "fluorophore" refers to a moiety that is capable of fluorescence, i.e. a moiety that absorbs light energy of a specific wavelength and re-emits light at a longer wavelength. Exemplary fluorophores include, but are not limited to, fluoresceins, rhodamines, coumarins, phthalocyanines, porphyrins, pyrenes, cyanines, squaraines, and boron-dipyrromethenes. The term "fluorophore" includes near-infrared dyes that absorb energy in the near-IR region (i.e. about 700 nm to about 1000 nm). Fluorophores may be attached to the remainder of a compound of formula (I), for example, by using a reagent comprising both a fluorescent moiety and a reactive group such as a carboxylic acid, an isothiocyanate, a maleimide, or an ester such as a succinimidyl, pentafluorophenyl or tetrafluorophenyl ester. Such groups may react with a group present on a precursor to a compound of formula (I), such as the primary amino group on Compound 2 shown in FIG. 1, to link the fluorescent moiety to the remainder of the compound of formula (I). As used herein, the term "fluorophore" encompasses both the fluorescent moiety itself and additional atoms or groups of atoms derived from the fluorescent reagent used to prepare the compound. For example, a reaction of a compound X—NH$_2$ with fluorescein isothiocyanate will produce a compound X—NH—C(S)—NH-fluorescein. Thus, the term "fluorophore" is intended to not only encompass the fluorescent moiety itself (e.g., fluorescein) but also the —C(S)—NH— linking atoms. Other fluorescent reagents include additional linking atoms between the fluorescent moiety and the reactive moiety, such as methylene groups (—CH$_2$—), carbonyl groups (—C(O)—), thiocarbonyl groups (—C(S)—), amino groups (—NH—), and combinations thereof, which are encompassed by the term "fluorophore" as the term is used herein.

As used herein, the term "subject" is intended to include human and non-human animals. Exemplary human subjects include a human patient having a disorder, e.g., cancer, or a normal subject. The term "non-human animals" includes all vertebrates, e.g., non-mammals (such as chickens, amphibians, reptiles) and mammals, such as non-human primates, domesticated and/or agriculturally useful animals (such as sheep, dogs, cats, cows, pigs, and the like), and rodents (such as mice, rats, hamsters, guinea pigs, and the like).

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

2. Methods

The disclosure provides methods of detecting a type III intermediate filament protein in a subject, methods of detecting a gliotic condition in a subject, methods of detecting myofibroblasts in a subject, and methods of probing mitochondrial structure and dynamics in a cell. Methods comprise administering to the subject or contacting the cell with compounds of formula (I).

a. Compounds of Formula (I)

Compounds that may be used as probes in the methods described herein include compounds of formula (I):

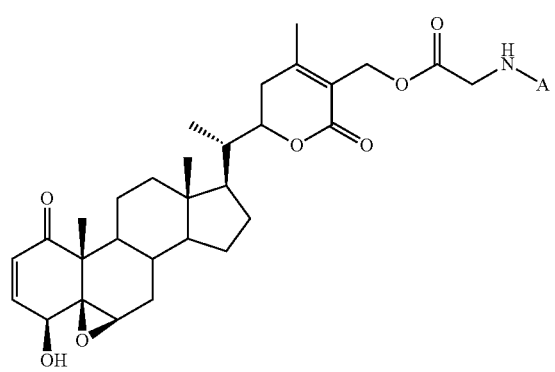

(I)

wherein A is a fluorophore.

Compounds of formula (I) are based on withaferin A (WFA), which is a small molecule that exerts potent antifibrotic activity by directly binding to the soluble form of the type III intermediate filament (IF) protein vimentin. WFA is derivatized with a glycine moiety, which is then coupled to a fluorophore.

Fluorophores that can be used in the compounds of formula (I) include fluoresceins, rhodamines, coumarins, phthalocyanines, porphyrins, pyrenes, cyanines, squaraines, and boron-dipyrromethenes. As further described below, fluorophores can be incorporated into compounds of formula (I) by using reagents that include the fluorophore and one or more reactive moieties, such as N-succinimidyl esters, which react with a primary amine on the precursor to the compound of formula (I). For example, fluorescent dye reagents that are commercially available include but are not limited to: 5- and 6-carboxyfluoresceins and esters thereof; fluorescein isothiocyanate (e.g., fluorescein-5-isothiocyanate or fluorescein-6-isothiocyanate); BODIPY® dyes commercially available from Molecular Probes; Alexa Fluor® dyes commercially available from Molecular Probes; CyDye fluors commercially available from GE Healthcare Biosciences; HiLyte™ Fluor Dyes available from AnaSpec; VivoTag™ fluorophores available from PerkinElmer; CF™ Dyes available from Biotium (including near-infrared CF™ dyes); and IRDye® infrared dyes available from Li-Cor (e.g., IRDye 800CW).

Compounds of formula (I) may be synthesized as illustrated in FIG. 1, in which the following abbreviations are used: Fmoc=fluorenylmethyloxycarbonyl; DCC=N,N'-dicyclohexylcarbodiimide; DMAP=4-dimethylaminopyridine; DMF=N,N-dimethylformamide; BODIPY FL NHS Ester=2,5-dioxopyrrolidin-1-yl 3-(5,5-difluoro-7,9-dimethyl-5H-4λ,4,5λ4-dipyrrolo[1,2-c:2',1'-f][1,3,2]diazaborinin-3-yl)propanoate (CAS Number 146616-66-2); BODIPY TR-X NHS Ester=2,5-dioxopyrrolidin-1-yl 6-(2-(4-(5,5-difluoro-7-(thiophen-2-yl)-5H-4λ4,5λ4-dipyrrolo[1,2-c:2',1'-f][1,3,2]diazaborinin-3-yl)phenoxy)acetamido)hexanoate (CAS Number 217190-13-1); IR Dye 800CW NHS Ester=sodium 2-((E)-2-((E)-3-(2-((E)-3,3-dimethyl-5-sulfonato-1-(4-sulfonatobutyl)indolin-2-ylidene)ethylidene)-2-(4-sulfonatophenoxy)cyclohex-1-en-1-yl)vinyl)-1-(6-((2,5-dioxopyrrolidin-1-yl)oxy)-6-oxohexyl)-3,3-dimethyl-3H-indol-1-ium-5-sulfonate (CAS Number 956579-01-4).

The excitation and emission maxima for compounds 4, 6 and 8 respectively are 502/510 nm, 588/616 nm, and 778/794 nm.

In some embodiments, A is selected from the group consisting of:

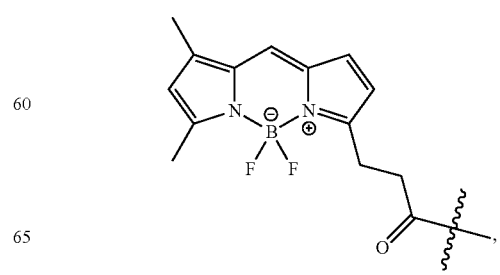

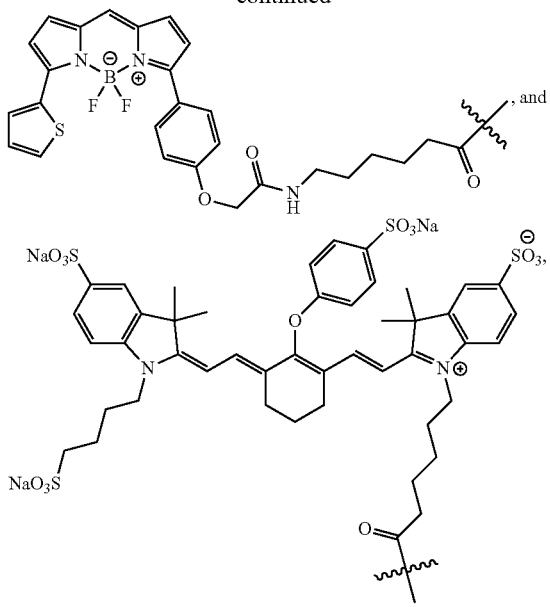

wherein ∿∿∿ represents the point of attachment to the nitrogen atom in formula (I).

b. Methods of Detecting Type III IF Proteins

In one aspect, the disclosure provides a method of detecting a type III intermediate filament protein in a subject. The method comprises administering to the subject a compound of formula (I) as described above, obtaining a tissue sample from the subject, and detecting the compound of formula (I) in the sample using fluorescence or near-infrared imaging.

The compound can be administered by any suitable route. For example, the compound can be administered via parenteral administration, which includes modes of administration that include intravenous, intramuscular, intraperitoneal, intradermal, intrasternal, subcutaneous and intraarticular injection and infusion. In some embodiments, the compound is administered intraperitoneally. In some embodiments, the compound can be administered via intraocular, intravitreal, subconjunctival, subscleral or topical administration, or can be administered using a drug delivery implant.

In some embodiments, the subject is a mammal, such as a human.

In some embodiments, the type III intermediate filament protein is vimentin or glial fibrillary acidic protein (GFAP). Type III IF proteins support the cellular membranes, keep some organelles in a fixed place within the cytoplasm, and transmit membrane receptor signals to the nucleus. Vimentin is the most widely distributed of all IF proteins, can be found in fibroblasts, leukocytes, and blood vessel endothelial cells. GFAP is found in astrocytes and other glia. Vimentin overexpression is associated with irreversible fibrotic outcomes in the cornea and its deficiency is protective against scarring.

c. Methods of Detecting Myofibroblasts

In one aspect, the disclosure provides a method of detecting myofibroblasts in a subject. The method comprises administering to the subject a compound of formula (I) as described above, obtaining a tissue sample from the subject, and detecting the compound of formula (I) in the tissue sample using fluorescence or near-infrared imaging.

Development of corneal fibrosis from overexpression of IF proteins in myofibroblasts can cause blindness. Detection of myofibroblasts can therefore serve as an early marker of pathologies such as fibrosis or other injury, e.g., in eye tissue.

In some embodiments, the gliotic condition is selected from the group consisting of choroidal neovascularization, diabetic retinopathy, glaucoma, epiretinal membranes and vitreoretinopathy.

In some embodiments, the subject is a mammal, such as a human.

d. Methods of Probing Mitochondrial Structure and Dynamics

In one aspect, the disclosure provides a method of probing mitochondrial structure and dynamics in a cell. The method comprises contacting the cell with a compound of formula (I) as described above, and detecting the compound of formula (I) in the cell using fluorescence or near-infrared imaging.

As described herein, the present disclosure has multiple aspects. These aspects and their embodiments are further illustrated by the following non-limiting examples.

3. Examples

The following examples are presented for purposes of illustration and are not intended to limit the scope of the disclosure.

Materials and Methods.

Certain experimental details are provided in the below examples.

Laser Injury Model of Choroidal Neovascularization (CNV).

Mice of both sexes were anesthetized and subjected to 4 equally spaced laser burns focused on the retinal pigment epithelium (RPE). Using the Meridian laser attached to Micron III retinal fundus microscope (Phoenix Research labs) we used strong injury (150 mW with 50 msec pulse) to promote retinal gliosis with CNV.

Abbreviations.

BHK-21 cells: Baby Hamster Kidney cells; RbCF cells: Rabbit Corneal Fibroblasts.

EXAMPLE 1

Synthesis of Probe Compounds

Probe compounds WFA-Verde, WFA-Rosa and WFA-IRDye800CW were prepared as generally illustrated in FIG. 1, and as described below.

Synthesis of the Intermediate Compound 2.

To Withaferin A (compound 1) (100 mg, 0.212 mmol) dissolved in DMF (5 mL) was added Fmoc-Gly-OH (69.3 mg, 0.233 mmol), DCC (48.0 mg, 0.233 mmol), DMAP (1.29 mg, 0.011 mmol) and stirred under argon at rt overnight. The reaction mixture was diluted with water (20 mL) and extracted with ethyl acetate (2×20 mL). The combined organic extracts were dried ($Na_2SO_4$) and concentrated. Purification by flash chromatography on silica gel (Hexane/EtOAc 70:30) provided Fmoc-Glycine conjugated Withaferin A. Deprotection of the Fmoc group was carried out using piperidine in DMF. To Fmoc-Glycine conjugated Withaferin A (11 mg, 0.0147 mmol), piperidine (1.38 mg, 0.0161 mmol)/DMF (0.25 mL) solution was added and stirred at rt for 15 min. Later the solution was dried under vacuum overnight to provide the intermediate compound 2, which was used immediately without any further purification for the subsequent coupling reactions.

General Synthesis of Probes 4, 6 and 8.

The appropriate NHS ester (BODIPY FL NHS Ester, BODIPY TR-X NHS Ester, IR Dye 800CW NHS Ester) (5 mg, 1 eq.) was dissolved in 0.5 mL DMF and the solution was added to the intermediate amine compound 2 (1 eq.) and stirred at 32° C. for 48 h. The reaction mixture was concentrated under vacuum for 48 h to remove DMF. Purification using HPLC on C18 silica gel column (gradient ACN/$H_2O$ system) provided the desired probes.

Characterization Data for Withaferin A-BODIPY-FL (or WFA-Verde) 4.

$^1$H NMR (500 MHz, $CDCl_3$) δ 7.10 (s, 1H), 6.94 (dd, J=5.7, 9.9 Hz, 1H), 6.90 (d, J=3.7 Hz, 1H), 6.30 (d, J=3.9 Hz, 1H), 6.22 (d, J=10 Hz, 1H), 6.14 (s, 1H), 6.07 (t, J=6.3 Hz, 1H), 4.98 (q, J=11.6 Hz, 2H), 4.42 (dt, J=13.2, 3.7 Hz, 1H), 4.03 (dd, J=3.8, 3.8 Hz, 2H), 3.79 (d, J=5.8 Hz, 1H), 3.51 (br s, 1H), 3.30 (t, J=7.5 Hz, 2H), 3.25 (br s, 1H), 2.71 (t, J=7.6 Hz, 2H), 2.58 (s, 3H), 2.53 (m, 1H), 2.45 (br s, 1H), 2.27 (s, 3H), 2.24 (m, 1H), 2.17 (m, 2H), 2.08 (s, 3H), 2.01 (m, 3H), 1.85 (m, 1H), 1.7 (m, 3H), 1.43 (s, 3H), 1.14 (m, 3H), 1.01 (d, J=6.5 Hz, 3H), 0.90 (t, J=6.5 Hz, 2H), 0.72 (s, 3H); $^{13}$C NMR (125 MHz, $CDCl_3$) δ 202.3, 171.9, 169.7, 165.2, 157.7, 141.8, 132.3, 128.2, 123.8, 121.5, 120.5, 117.3, 78.3, 69.9, 63.9, 62.7, 58.8, 56.1, 52.0, 47.7, 44.2, 42.6, 41.3, 39.4, 38.8, 35.7, 31.2, 30.2, 29.8, 29.7, 27.3, 24.6, 24.3, 22.2, 20.7, 17.5, 14.9, 13.3, 11.6, 11.3; LRMS (ESI, M$^+$-HF) m/z 782.5 (calculated for $C_{44}H_{54}BFN_3O_8$, 782.4). A 75 min gradient elution was used [25-100% acetonitrile (ACN) with 0.1% formic acid] to obtain LC-MS data.

Characterization Data for Withaferin A-BODIPY-TR-X (or WFA-Rosa) 6.

$^1$H NMR (500 MHz, $CDCl_3$) δ 8.14 (d, J=3.8 Hz, 1H), 8.02 (d, J=8.8 Hz, 2H), 7.52 (d, J=5.1 Hz, 1H), 7.23 (s, 1H), 7.20 (dd, J=4.0, 4.0 Hz, 1H), 7.14 (d, J=4.2 Hz, 1H), 7.11 (d, J=4.4 Hz, 1H), 7.07 (d, J=8.8 Hz, 2H), 6.97 (dd, J=9.9, 5.7 Hz, 1H), 6.86 (d, J=4.2 Hz, 1H), 6.71 (m, 2H), 6.24 (d, J=10 Hz, 1H), 5.98 (t, J=5.5, 5.5 Hz, 1H), 4.98 (q, J=11.7 Hz, 2H), 4.61 (s, 2H), 4.42 (dt, J=13.0, 3.5 Hz, 1H), 3.99 (dd, J=3.5, 3.5 Hz, 2H), 3.80 (d, J=5.8 Hz, 1H), 3.42 (q, J=6.4 Hz, 2H), 3.28 (br s, 1H), 2.54 (m, 2H), 2.22 (m, 4H), 2.09 (s, 3H), 2.08 (m, 1H), 1.98 (m, 1H), 1.88 (m, 1H), 1.69-1.47 (m, 6H), 1.46 (s, 3H), 1.40-0.95 (m, 9H), 1.03 (d, J=6.6 Hz, 3H), 0.93 (t, J=6.8 Hz, 2H), 0.74 (s, 3H); HRMS Pos. Mode (ESI, M$^+$+Na) m/z 1069.4363 (calculated for $C_{57}H_{65}BF_2N_4NaO_{10}S$, 1069.4380).

Characterization Data for Withaferin A-IRDye 800CW 8.

FIRMS Neg. mode (ESI, [M-3Na]73) m/z 502.8396 (calculated for $C_{76}H_{90}N_3O_{21}S_4$, 1508.4950, [M-3Na]$^-$/3: 502.8317). Also observed a minor peak [M-3Na+H]$^-$/2 m/z 754.7526 (calculated for $C_{76}H_{91}N_3O_{21}S_4$, 1509.5028, [M-3Na+H]$^-$/2: 754.7514).

EXAMPLE 2

Labeling Vimentin in Cell Cultures

Rabbit corneal fibroblast cells were plated in glass bottom culture plates (MatTek, MA) for 18 h, washed and incubated with a high dose of 3.5 µM WFA-Verde (Left panel, green) for 1 h in well spread cells. Cells were fixed, permeabilized, and prepared for immunohystochemistry (IHC) analysis. Cells were probed with anti-pSer38Vimentin antibody (Central panel, Red), and counterstained with DAPI to mark nuclei (blue). p-Ser38Vimentin and WFA-Verde show extensive co-localization, as shown in the merged image as detected by epifluorescence microscopy; see FIG. 2.

Figure 2:
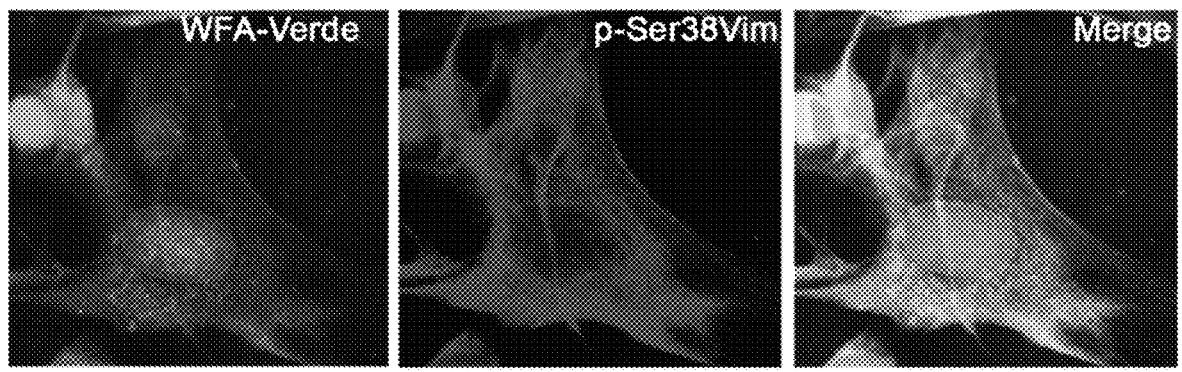
FIG. 2 shows fluorescence images of cells following exposure to a compound described herein, as further described in Example 2.

There is considerable overlap of WFA-Verde staining of cytoskeletal structures as well as detection of numerous fine particles revealing that the WFA probe does label both soluble and vimentin structures throughout the cell cytoplasm (FIG. 2). The short exposure to the higher dose of WFA-Verde did not dramatically alter the cytoskeleton in well spread cells.

EXAMPLE 3

Live Cell Target Detection and Dynamic Imaging

Soluble vimentin is a broad definition for the biochemical properties of vimentin forms that are extracted in low salt buffers (composed of tetramers, short oligomers, unit length filaments etc.). As such, these soluble vimentin forms are more dynamic structures. We employed a genetic approach to introduce a hybrid mCherry-vimentin construct to express vimentin as a fusion protein with the red fluorescent protein mCherry.

Figure 3:
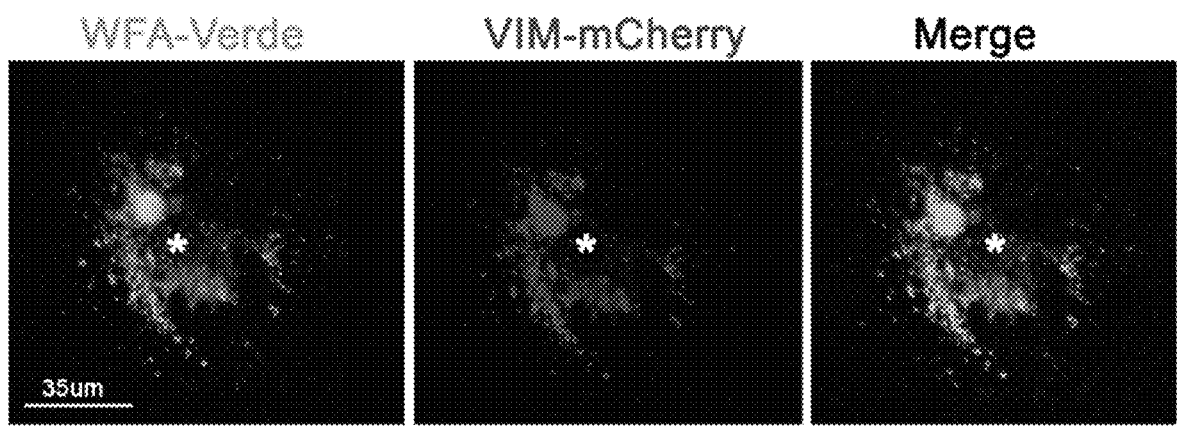
FIG. 3 shows fluorescence images of cells following exposure to a compound described herein, as further described in Example 3.

BHK-21 cells were transiently transfected with pmCherry-vimentin-N-18 plasmid (Adgene, MA) using lipofectamine, according to vendor instructions. Cells were trypsinized and replated in glass bottom culture plates (MatTek, MA) for 1 h in complete DMEM medium. Cells were washed once with SF-DMEM and incubated with 250 nM WFA-Verde (green) for 5 min and washed to remove unbound probe. Cells were immediately imaged live by epifluorescence microscopy, without fixation. See FIG. 3. WFA-Verde (left panel, green) binds to soluble vimentin forms and shows co-localization with Vim-Cherry (central panel, red), as revealed in the merged image (right panel). Asterisks mark the position of the nucleus. The expression of mCherry-vimentin and WFA-Verde bound protein targets was observed under fluorescence with dual excitation in the red and green channels, respectively. The mCherry-vimentin expression, as anticipated, was observed as red dots (soluble precursors) and showed the co-labeling with the green WFA-Verde probe in these early spreading cells. This result demonstrated that the WFA-Verde probe binds and labels soluble vimentin very efficiently.

EXAMPLE 4

Dynamic Movement of Vimentin Structures

In certain experiments, WFA-Verde when added to cells bound soluble vimentin rapidly and caused them to form small aggregates that led to loss of their dynamic motility. This problem poses a challenge as it prevents one from studying the dynamic movements of vimentin in cells using live cell imaging. This apparent problem for cell imaging was not predicted a priori and was also not due to the chemical structure of WFA-Verde compound per se because use of the WFA-BODIPY probe that contained a longer linker, WFA-Rosa, also caused ligand-bound soluble filaments to aggregate and lose dynamic motility (data not shown). However, we discovered that presence of serum dramatically alters how WFA-Verde or WFA-Rosa affects the bound vimentin forms because wash out of serum and performing imaging in serum-free (SF) medium overcomes this problem. So using SF medium in experiments, one is able to visualize soluble vimentin often observed as short filaments called "squiggles" at the cell periphery of polarized cells. Importantly, one may also wish to image cells live and detect the dynamic movements of these squiggles and related longer IF structures. It is known that when cells become polarized cells they maintain strong cytoskeletal vimentin attached to the perinuclear region, and the spread cytoplasmic region extending to the plasma membrane shows extensive short and squiggle structures.

Figure 4:
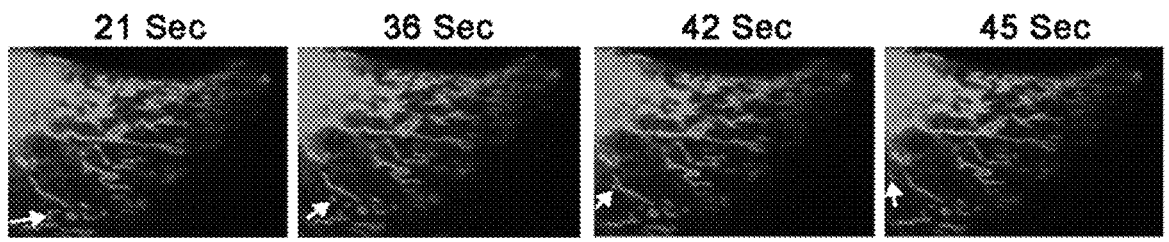
FIG. 4 shows fluorescence images of cells following exposure to a compound described herein, as further described in Example 4.

BHK-21 cells were plated in glass bottom culture plates for 18 h to promote spreading. Cells were washed to remove serum and then incubated with 250 nM WFA-Verde (green) in SF medium for 5 min, washed once, and immediately imaged live by epifluorescence microscopy. Images were collected at 5 sec intervals, and arrows follow WFA-Verde labeled dot-like structures over time. See FIG. 4. The representative dot moves at a speed of ~0.5 μm/sec, which is in the range with other reports that used vimentin-Green fluorescent protein hybrid expression (GFP-vimentin vectors) (Prahlad V et al. (1998). Rapid movements of vimentin on microtubule tracks: kinesin-dependent assembly of intermediate filament networks. *J Cell Biol* 143: 159-170).

These data demonstrate that WFA-Verde can also bind and capture the dynamic behaviors of IFs in living cells. These data also corroborate previous investigations by others who used GFP-vimentin hybrid expression studies to show similar dynamic movements of vimentin squiggles in living cells. As the experimental model is simple and can be applied to any type of mammalian cell with no special genetic manipulation, any biological or cellular process can be investigated in this system with WFA-Verde or WFA-Rosa probes.

EXAMPLE 5

In Vivo Delivery of Probes for Fibrosis Target Binding Studies

Alkali injury to the cornea causes blindness due to the development of corneal fibrosis from overexpression of IF proteins in resident myofibroblasts. This model is extensively employed to investigate corneal fibrosis and role of IF proteins. A direct method to demonstrate WFA probes bind to overexpressed vimentin in the corneal stroma in vivo has been established previously.

Figure 5:
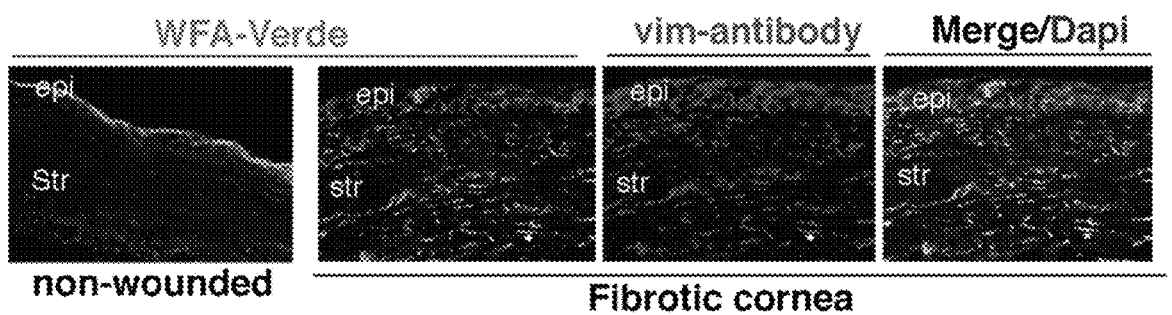
FIG. 5 shows fluorescence images of tissue sections following exposure to a compound described herein, as further described in Example 5.

Thus, anesthetized mice were injured with alkali by application of 0.15N NaOH for 1 min to the cornea, eyes was extensively and the corneal epithelium gently removed. During the process of wound healing the resident keratocytes become activated into wound fibroblasts and subsequently into myofibroblasts to overexpress both vimentin and desmin, the two type III IFs in the cornea. Thus, heightened expression of these IF targets compared to uninjured corneas, the latter expressing very low levels of vimentin and no desmin, provided the rationale to compare uninjured mice. After 14 days, injured mice as well as non-injured mice were injected with WFA-Verde by intraperitoneal delivery. Mice were sacrificed after 1 h, eyes enucleated and cryosections were obtained. Tissue sections were fixed and stained for vimentin using secondary antibody with complementary color to the green WFA-Verde probe. See FIG. 5. Images of non-injured corneas revealed very low level of background staining in the corneal stroma with autofluorescence in the corneal epithelium. On the other hand, staining of corneas from injured eyes showed an abundance of WFA-Verde binding to corneal myofibroblasts illuminating the extensive fibrotic cells present in the tissue. This staining also showed some intensity variation possibly due to differences in target protein expression levels, which was revealed by examining the vimentin staining with antibody detection. There was extensive overlap between vimentin antibody staining and WFA-Verde binding in majority of cells that were labeled. These data proved that we have overcome a number of challenges that present with development of biomarker imaging probes. The first is that WFA-Verde was systemically delivered and reached the target organ in 1 h. The second achievement is a good amount of the compound was taken up and was likely also not metabolically converted as it retained target binding. The third achievement is WFA-Verde was retained in the targeted cells bound to IF proteins and also retained fluorescence of BODIPY after tissue fixation and processing. The achievement here has allowed us to examine co-labeling with vimentin antibody, but moreover, very high-resolution cellular imaging can be performed in targeted organs. This will be very useful in drug development paradigms that want to investigate cellular specificity of drug action in complex multi-cellular organs where IFs have been focused as biomarkers of pathology (fibrosis, cancer, injury etc.).

EXAMPLE 6

Binding and Labeling GFAP

Figure 6:
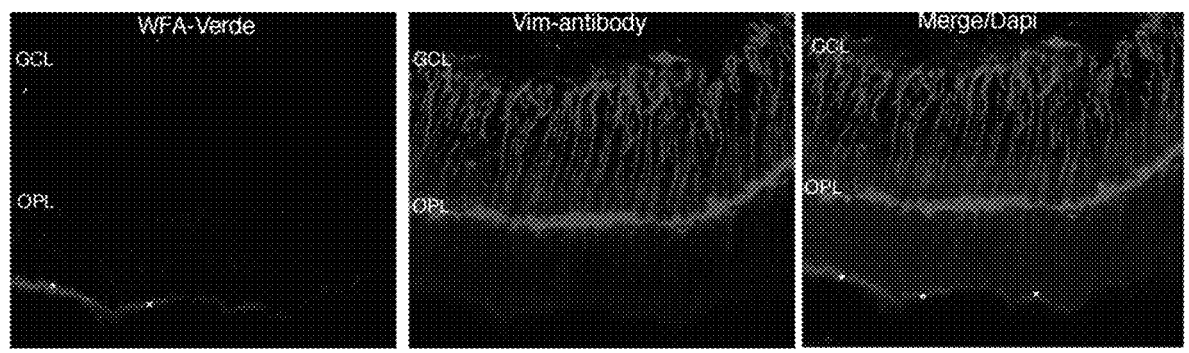
FIG. 6 shows fluorescence images of tissue sections following exposure to a compound described herein, as further described in Example 6.

Non injured mice were injected with WFA-Verde (1 μM) via intraperitoneal delivery and eyes enucleated after 24 h. Cryosections of the eye were subjected to fixation and subsequently stained with anti-vimentin antibody (V9) to mark Muller glial filaments. Imaging of the same tissue in FITC channel reveals only background autofluorescence (asterisks) from retina revealing minimal incorporation of the WFA-Verde probe into vimentin in non-gliotic tissues. See FIG. 6.

EXAMPLE 7

In Vivo Delivery of Probes for Retinal Gliosis Studies

One of the most challenging areas of probe development is the delivery of small molecules to the central nervous system because many probes do not cross the blood brain or blood retinal barrier. For WFA-Verde, or any of WFA based analogs, to be useful in CNS applications, prediction of delivery to these CNS target tissues to bind and label IFs cannot be predicted. The enablement of this application is thus important for use in any disease and injury-related biomarker-imaging paradigm. To demonstrate that delivery of WFA-Verde or WFA-Rosa and achieve in vivo target binding in the injured retina we chose a mouse model that is widely employed to study choroidal neovascularization (CNV) in age-related macular degeneration (AMD). In mice, laser injury to the posterior retinal pigment epithelium (RPE) affords one to examine the course of injury response leading to choroidal blood vessels invading the retina. This model of retinal injury induces reactive gliosis with the overexpression of type III IF proteins vimentin and glial fibrillary acidic protein (GFAP) being hallmarks of this process. GFAP and vimentin become the prominent cytoskeletal filaments in Muller glia as their structures not only define the processes of Muller cells but these proteins are abundant as well. Thus, Muller glial cells have functions both as structural and stress sensors in the retina that communicate directly via their long cellular processes across the entire thickness of retina from the vitreal surface to the photoreceptor cells. Laser injury induces retinal gliosis and CNV in mouse retinas to afford the simultaneous detection of vimentin in invasive choroidal blood vessels and differentiating RPE that invade the inner retina as myofibroblasts along with these IF proteins in Muller glia.

Figure 7:
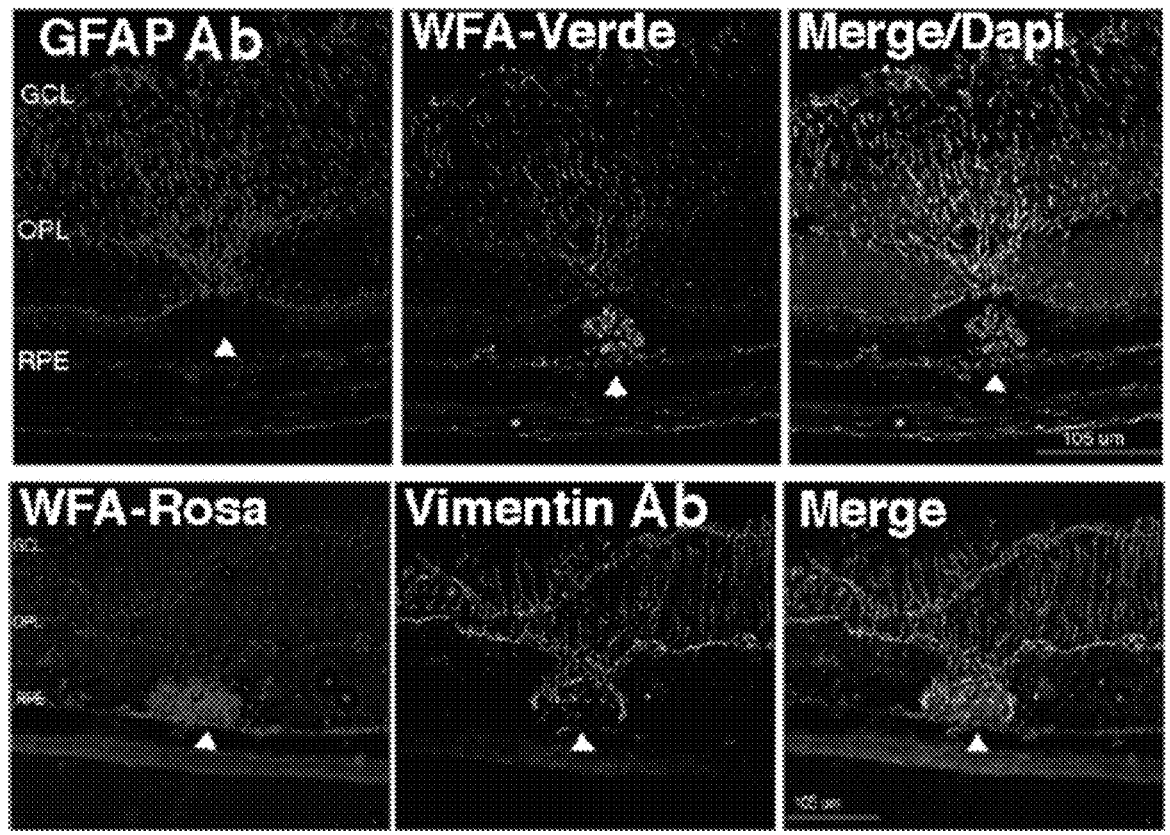
FIG. 7 shows fluorescence images of tissue sections following exposure to a compound described herein, as further described in Example 7.

This multi complex cellular involvement that leads to retinal scarring was modeled in laser injury experiments. The mouse imaging system (Micron III, Phoenix Research Labs, CA) provided with an image-guided Meridian Merilas 532 nm (Nd:YVO) laser was employed. Using the Diode laser 625-645 nm as an aiming beam the continuous wave, KTP frequency doubled Nd:YVO 532 nm laser was employed to deliver laser injuries in anesthetized mice. Here four (150 mW; 10-µm diameter, 50 msec duration) laser shots equally spaced around the optic nerve were delivered to disrupt the RPE. After mice recovered for 7 days, 1 µM of WFA-Verde or 1 µM WFA-Rosa was delivered by intraperitoneal delivery to different mice. Mice were sacrificed 24 h later and eyes enucleated for tissue sectioning and antibody staining to vimentin and GFAP. See FIG. 7.

WFA-Verde labeled the Muller glia extensively in the region where the laser lesion was localized with overlap on GFAP-containing filaments and illuminated also bundles of endothelial cells of the invasive blood vessels. Many RPE cells we also labeled intensively suggesting they had upregulated vimentin expression to form the fibrovascular scar tissue that develops. WFA-Rosa showed a similar pattern illuminating Muller glia and overlapping with vimentin in Muller glia as well as robustly labeling the invasive blood vessel endothelial cells and RPE differentiating in the vicinity of the laser lesion. Together, these probes showed efficient binding to vimentin and GFAP in the laser lesion regions and demonstrated for the first time that delivery by systemic methods afforded the labeling of retina in a gliotic condition of very high clinical relevance to CNV in AMD patients. This is the first demonstration of in vivo targeting and labeling of this class of protein in the CNS.

EXAMPLE 8

Sensing Mitochondrial Structure and Dynamics

Vimentin has numerous cellular functions as this protein class is highly complex in its dynamics and expression. One such function is an association of certain vimentin forms with mitochondria, but this fraction of vimentin-associated with mitochondria is only a subset of the bulk of cytoplasmic vimentin. Using transfection studies, full-length vimentin-green fluorescent protein hybrid constructs when transfected into fibroblasts identified vimentin filamentous structures that show partial overlap in staining properties with that produced by MitoTracker® labeling as anticipated. These data suggest that although mitochondria associate with vimentin, numerous vimentin species remain non-associated with mitochondria. The mechanism of how these selected vimentin forms become associated with mitochondria is not known. However, it is known that when the N-terminal amino acid residues 1-138 of vimentin when tagged to GFP and transfected into cells the GFP staining showed distinct overlap with MitoTracker® dye staining (specific for staining mitochondria). These studies also revealed that the unique properties of the mitochondrial-associated vimentin reside in the N-terminal 40-93 amino acid domain (*Mol Biol Cell*. 2011 Jul. 1; 22(13):2282-9). This genetic approach that used the 1-138 amino acid domain of vimentin to cause the mitochondrial-interacting function of vimentin to be illuminated via GFP tagging, however, also necessitated that the bulk of vimentin does not polymerize because this vimentin N-terminal domain essentially prevents vimentin polymerization (*J Cell Sci* 122, 2914-2923). Thus cells expressing only vimentin 1-138 domain virtually lack the non-mitochondrial associated majority of cytoskeletal filaments to afford this result. This rather disruptive approach would not be desired means to investigate vimentin functions as numerous cytoskeletal functions of vimentin are also abrogated.

Figure 8:
FIG. 8 shows fluorescence images of cells following exposure to a compound described herein, as further described in Example 8.

BHK-21 cells were plated overnight and prior to staining placed in serum-free medium. Cells were incubated with MitoTracker® dye, washed to remove excess dye and then incubated with 250 nM WFA-Verde for 5 mins. Cells were washed and directly imaged live at dual wavelengths. See FIG. 8. The extensive overlap of vimentin stained structures with WFA-Verde and MitoTracker® dye is revealed in the panel showing the overlap.

It is known that WFA-Verde binds to the C-terminal cysteine residue in the rod 2B domain of vimentin, whereas, the mitochondrial-association domain of vimentin is in the N-terminus. Thus, our unprecedented discovery provides the means for distinguishing vimentin species that become associated with mitochondria at the low doses. In addition, using higher doses of WFA-Verde we show incorporation of the probe into the bulk of the cytoskeletal vimentin overlapping with the serine 38 phosphorylated isoform of vimentin in rabbit corneal fibroblasts (Example 2). We also show that at low doses the remaining cytoskeletal forms of vimentin remain intact with WFA-Verde, and thus, this selective mitochondrial-associated staining is an advantage because it demonstrates a versatility of this probe. Thus, the fact that low dose WFA-Verde can bind and illuminate exclusively mitochondrial-associated structures (also labeled by the MitoTracker® dye) identify a novel enabling function of WFA-Verde.

Figure 9:
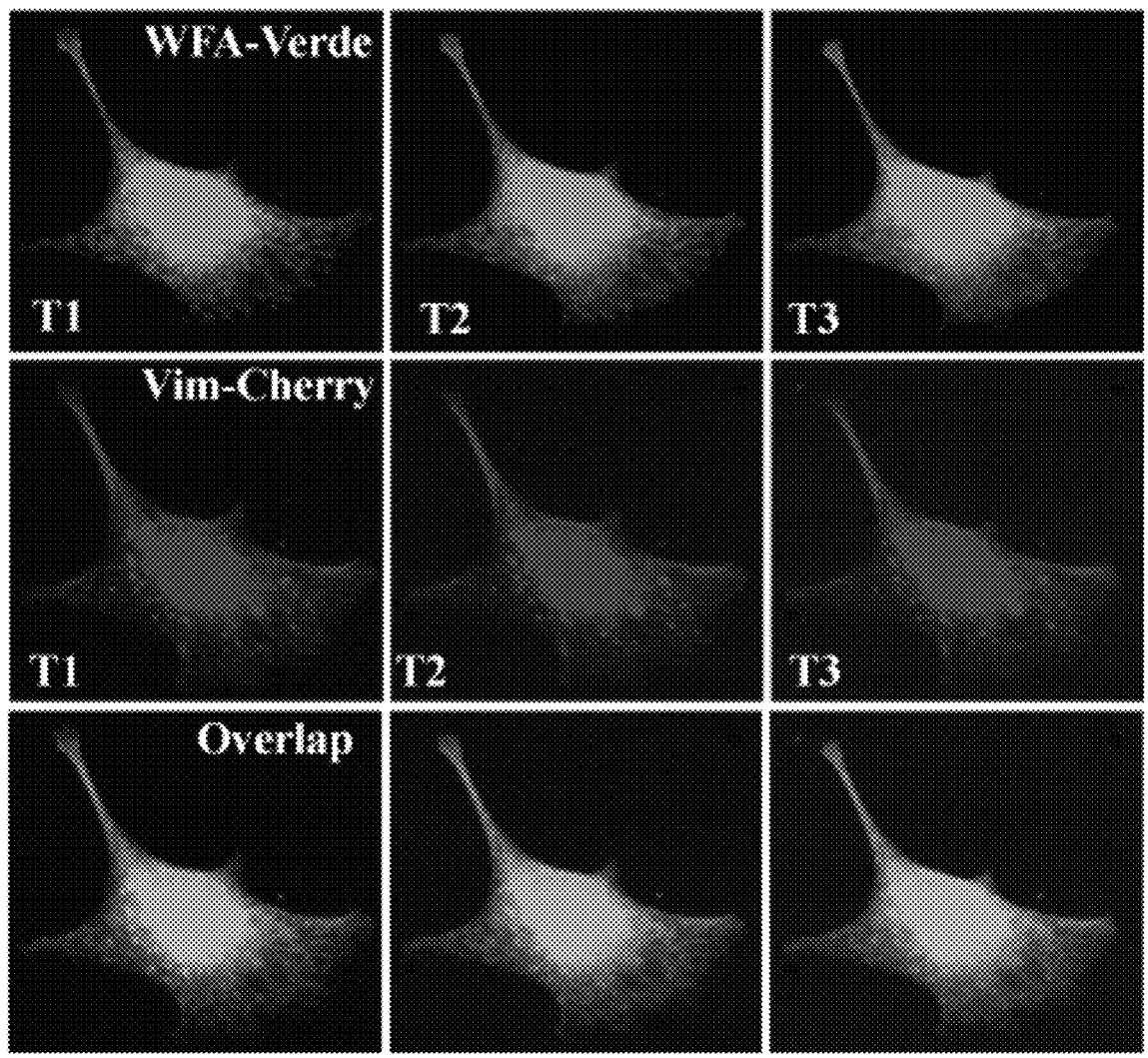
FIG. 9 shows fluorescence images of cells following exposure to a compound described herein, as further described in Example 8.

WFA-Verde at low dose does not stain to all vimentin structures. Transfection of human vimentin-cherry hybrid plasmid into fibroblasts and examination of polymerized vimentin structures under live cell imaging experiments identify numerous vimentin filaments that show some common, and yet, other distinct staining from the WFA-Verde-labeled structures. BHK-21 cells were transiently transfected with pmCherry-Vimentin-N-18 plasmid (Adgene, MA) using lipofectamine. Cells were cultured to establish the expression of plasmid and then trypsinzed and replated in glass culture plates for 18 h. Cells were washed in serum-free medium and incubated with 250 nM WFA-Verde for 5 minutes, washed and imaged in time-lapse series using 5 second intervals. Images at the starting point (T1), midpoint (T2) and at end of 3 minutes (T3). Numerous mCherry labeled dot-like structures also overlapped with WFA-Verde labeled dots and squiggles, but many long mCherry-labeled structures do not overlap. See FIG. 9.

These distinct subspecies of WFA-Verde-labeled vimentin structures overlapping also with certain exogenously expressed vimentin filaments, but not all filaments, reveals that the segregation of vimentin species to different cellular functions is governed by mechanisms intrinsic to different cell states. WFA-Verde could be employed as a probe to identify these mechanisms that regulate how vimentin is segregated into this distinct species that associates with mitochondria from the bulk of vimentin that remains broadly distributed and serves other functions. Hence drugs that perturb mitochondria directly or via their association with other cellular targets could exploit WFA-Verde to report altered mitochondrial dynamics.

Figure 10:
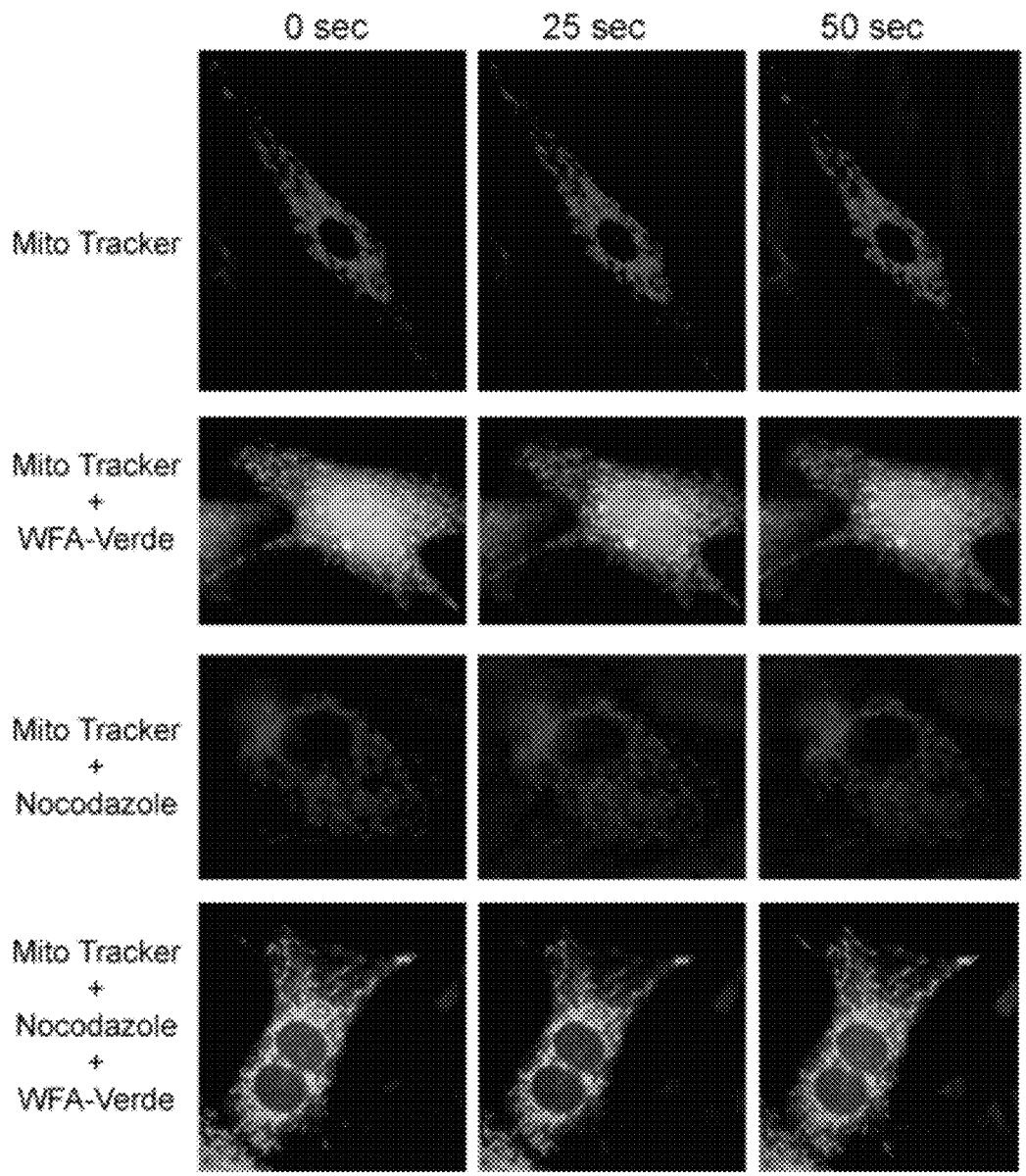
FIG. 10 shows fluorescence images of cells following exposure to a compound described herein, as further described in Example 8.

As one such example, using the microtubule drug nocodazole known to interfere with mitochondrial movements we show that this treatment not only alters MitoTracker® dye staining characteristics in time lapse live cell imaging studies, but also WFA-Verde staining demonstrating movement arrest of vimentin-stained structures over time. BHK-21 cells were cultured in glass bottom plates and treated with MitoTracker® dye alone or separately with 10 µM Nocodazole. In other experiments, MitoTracker® dye was added to cells and followed by WFA-Verde or MitoTracker® dye was added with 10 µM Nocodazole and then cells incubated with WFA-Verde. Time-lapse images were collected every 5 seconds in each of the four treatment groups. See FIG. 10. Nocodazole causes filaments to be arrested in movements showing also extensive overlap of WFA-Verde and MitoTracker® staining.

One of ordinary skill in the art of mitochondrial biology who has interests in understanding human mitochondrial dynamics in physiology and disease can now employ WFA-Verde or WFA-Rosa to bind and study the contribution of such vimentin subspecies responsible for targeting mitochondria.

EXAMPLE 9

Sensing Mitochondrial Structure and Dynamics

Figure 11:
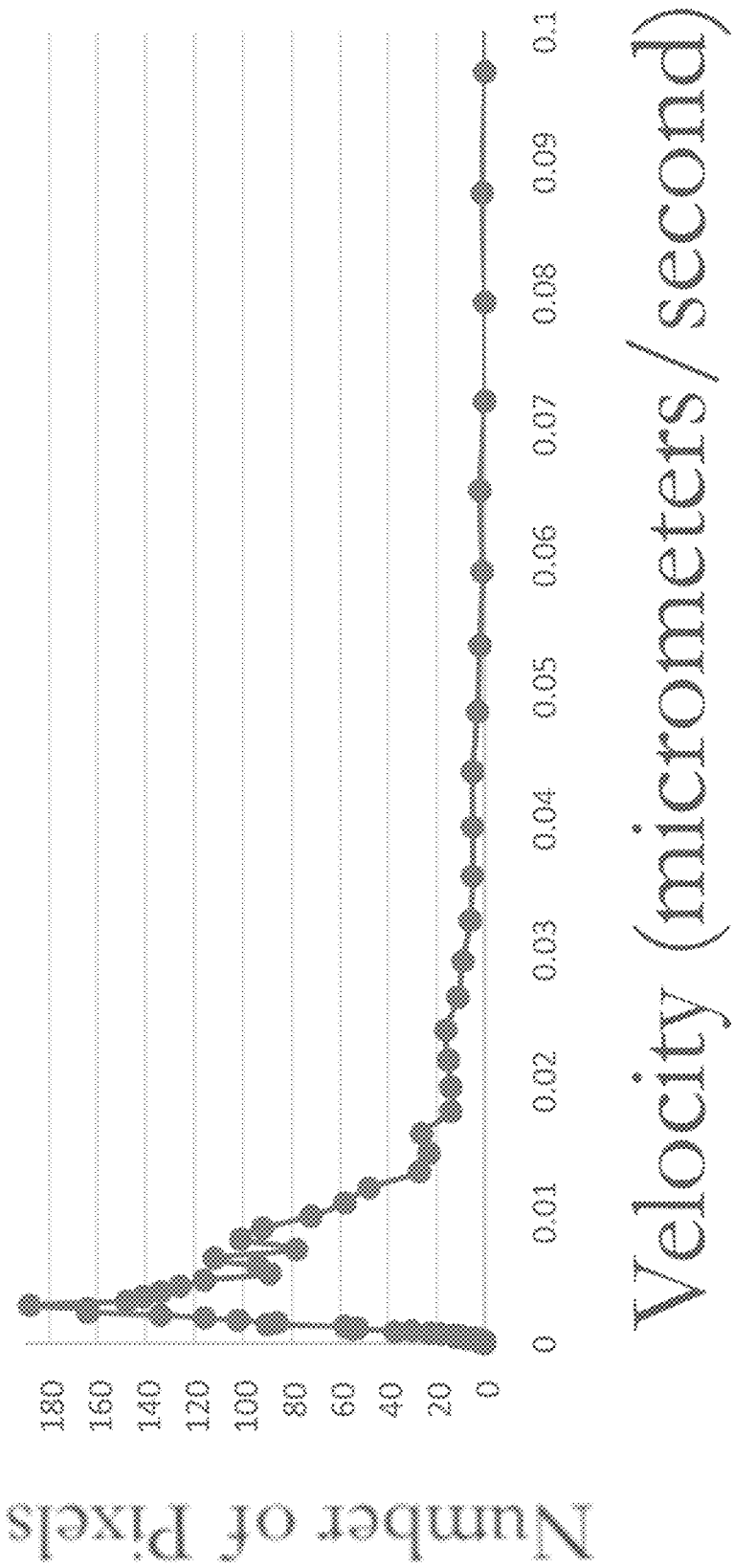
FIG. 11 shows velocity data for particles labeled with a compound described herein, as further descried in Example 9.
Figure 12:
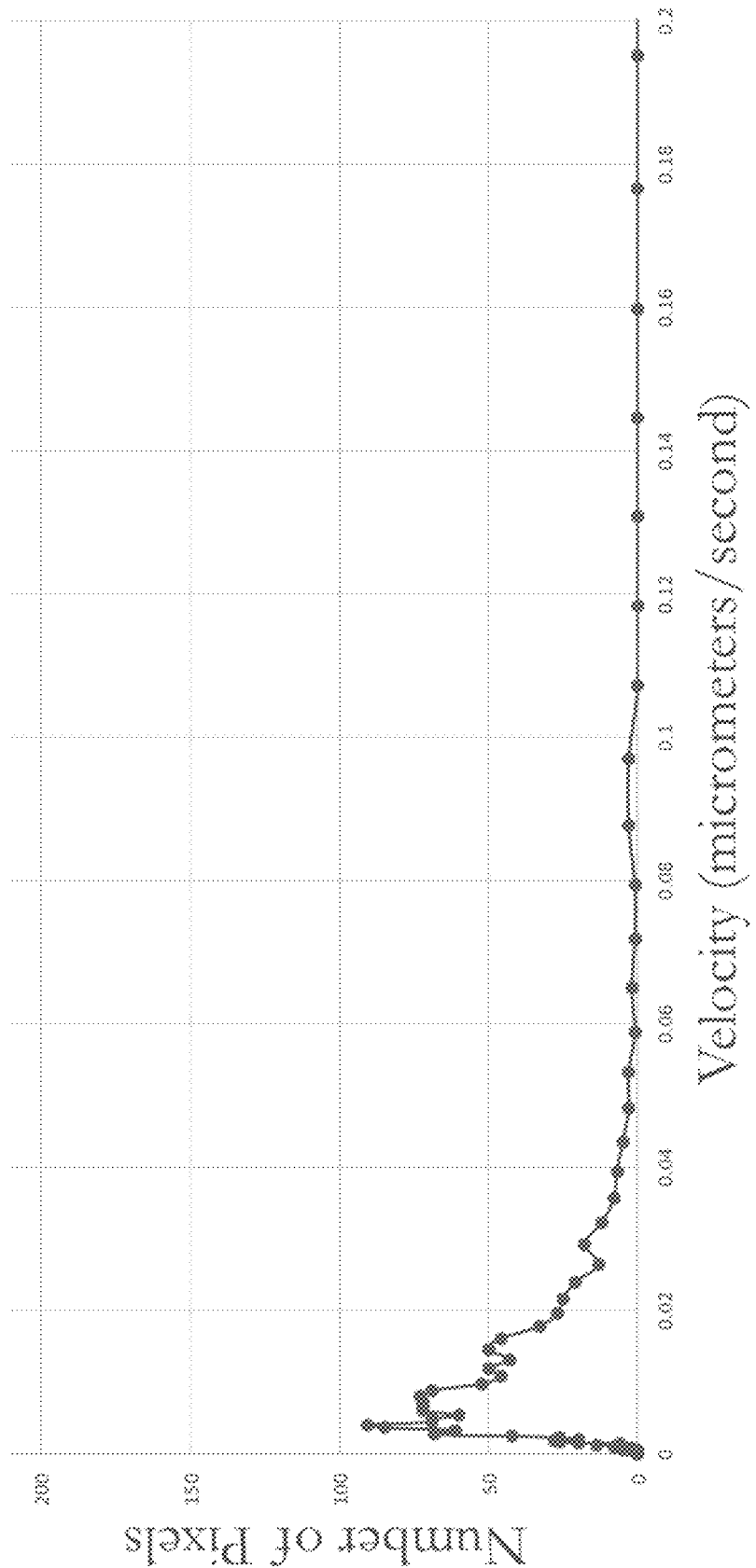
FIG. 12 shows velocity data for mitochondrial species labeled with MitoTracker® dye, as further described in Example 9.

Vimentin binds to mitochondria, an organelle that is highly dynamic and motile. In efforts to study vimentin-mitochondrial interactions, WFA-Verde has been employed to examine their motility characteristics. BHK-21 cells plated in glass-bottom dishes were incubated with 250 nM WFA-Verde, washed once, and immediately imaged live by epifluorescence microscopy. Images were collected at 5 sec intervals. Video time-lapse images were recorded and imported into FIJI/Image J software to quantify the motility of mitochondria following a published method (Miller et al. Automated Measurement of Fast Mitochondrial Transport in Neurons. *Frontiers in Cellular Neuroscience* 2015 Nov. 3; 9:435. doi: 10.3389/fncel.2015.00435. eCollection 2015). The pixel/frame values are converted to micrometers/second. The data show that the majority of motile WFA-Verde-labeled particles move at rates~0.01 micrometer/second (FIG. 11). This rate is similar to motility rates found using the Mito Tracker® dye in BHK-21 cells that labels mitochondria directly (FIG. 12). Taken together, the data shows that WFA-Verde tags soluble vimentin species bound to motile mitochondrial species efficiently. WFA-Verde can be used to obtain quantitative data from such motility measurement studies that could afford one the means to also interrogate biological and chemical conditions that perturb mitochondria motility through vimentin.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, dose alterations, or methods of use of the invention, may be made without departing from the spirit and scope thereof.

The invention claimed is:

1. A method of detecting a gliotic condition in a subject, comprising:
administering to the subject a compound of formula (I)

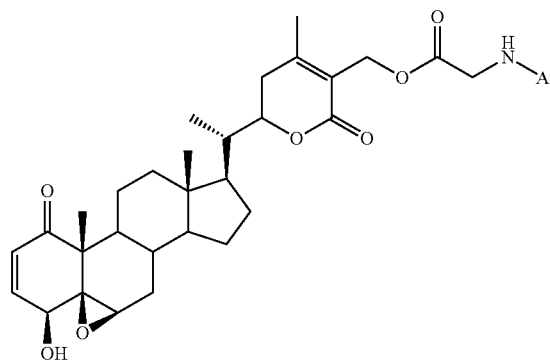

wherein:
A is a fluorophore;
obtaining a tissue sample from the subject; and
detecting the compound of formula (I) in the tissue sample using fluorescence or near-infrared imaging, thereby detecting a gliotic condition in the subject;
wherein the gliotic condition is selected from the group consisting of choroidal neovascularization, diabetic retinopathy, glaucoma, and vitreoretinopathy.

2. The method of claim 1, wherein the subject is a mammal.

3. The method of claim 1, wherein the compound binds a type III intermediate filament protein in an eye of the subject.

4. The method of claim 1, wherein A is:

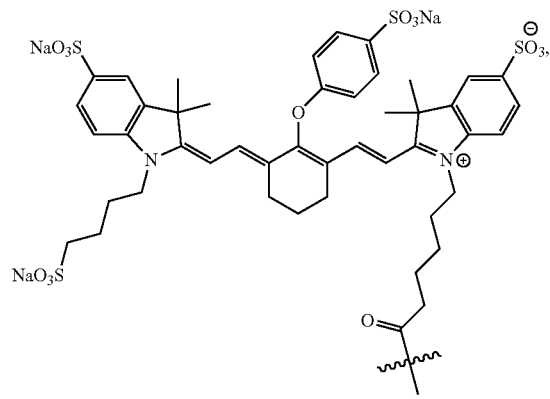

wherein ⌇⌇⌇ represents the point of attachment to the nitrogen atom in formula (I).

5. The method of claim 1, wherein A is a fluorophore selected from the group consisting of a fluorescein, a rhodamine, a coumarin, a pyrene, a cyanine, a squaraine, and a boron-dipyrromethene.

6. The method of claim 1, wherein A is a boron-dipyrromethene moiety derived from a boron-dipyrromethene N-hydroxysuccinimidyl ester.

7. The method of claim 1, wherein A is selected from the group consisting of:

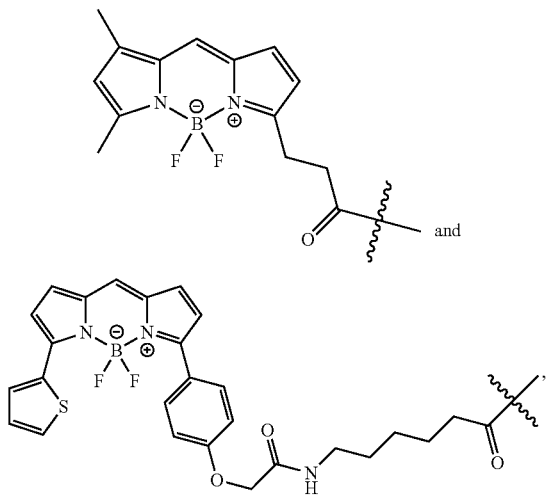

wherein ∿ represents the point of attachment to the nitrogen atom in formula (I).

8. The method of claim 1, wherein A is a near-IR dye selected from the group consisting of a cyanine, a squaraine, a phthalocyanine, a porphyrin, and a boron-dipyrromethene.

9. The method of claim 8, wherein the near-IR dye is a cyanine dye derived from a cyanine N-hydroxysuccinimidyl ester.

10. The method of claim 8, wherein A is:

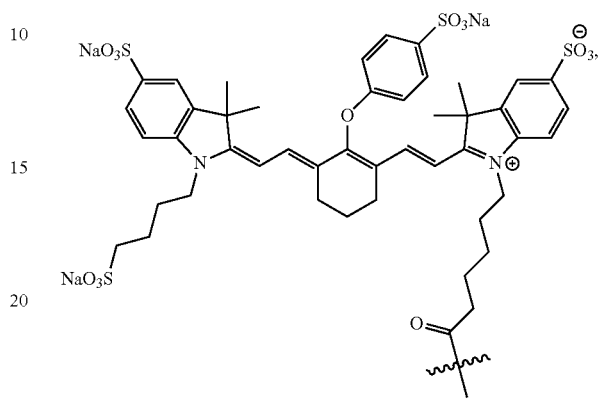

wherein ∿ represents the point of attachment to the nitrogen atom in formula (I).

11. The method of claim 1, wherein the compound of formula (I) is administered intraperitoneally.

12. The method of claim 1, wherein the tissue is a fibrotic tissue or gliotic tissue.

13. The method of claim 3, wherein the type III intermediate filament protein is vimentin or glial fibrillary acidic protein.

* * * * *